(12) United States Patent
Demharter et al.

(10) Patent No.: US 8,150,492 B2
(45) Date of Patent: Apr. 3, 2012

(54) CORRECTION METHOD AND MAGNETIC RESONANCE DEVICE

(75) Inventors: Nikolaus Demharter, Dormitz (DE); Michael Frank, Erlangen (DE); Sven Heggen, Erlangen (DE); Ernst Mustafa, Fürth (DE); Jürgen Rößler, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 300 days.

(21) Appl. No.: 12/386,328

(22) Filed: Apr. 16, 2009

(65) Prior Publication Data

US 2009/0270716 A1 Oct. 29, 2009

(30) Foreign Application Priority Data

Apr. 25, 2008 (DE) .................. 10 2008 020 781

(51) Int. Cl.
*A61B 5/0402* (2006.01)
*A61B 5/055* (2006.01)

(52) U.S. Cl. .................. 600/411; 600/413; 600/509

(58) Field of Classification Search .............. 600/411, 600/413, 509, 424
See application file for complete search history.

(56) References Cited

U.S. PATENT DOCUMENTS

| | | | | |
|---|---|---|---|---|
| 4,951,244 | A * | 8/1990 | Meyer | 708/290 |
| 7,221,973 | B2 * | 5/2007 | Nitz | 600/411 |
| 2007/0007960 | A1 | 1/2007 | King | |

OTHER PUBLICATIONS

Jacques Felblinger et al; Restoration of Electrophysical Signals Distorted by Inductive Effects of Magnetic Field Gradients During MR Sequences; Magnetic Resonance in Medicine 41:715-721; Magazine; 1999.

Freddy Odille et al; Noise Cancellation Signal Processing Method and Computer System for Improved Real-Time Electrocardiogram Artifact Correction During MRI Data Acquisition; IEEE Transactions on Biomedical Engineering, vol. 54, No. 4, Apr. 2007; Magazine; 2007.

* cited by examiner

*Primary Examiner* — Brian Casler
*Assistant Examiner* — Phong K Huynh

(57) ABSTRACT

The invention relates to a correction method for correction of noise resulting from gradient artifacts in ECG signal data records recorded in a magnetic resonance device by an ECG measuring apparatus. A first correction data record is determined with a reference point of the ECG measuring apparatus located at a first position in the magnetic resonance device. An ECG signal data record is measured with the reference point of the ECG measuring apparatus located at a second position in the magnetic resonance device. A modified correction data record is specified as a function of the first correction data record and the first and second position of the reference point. The ECG signal data record is corrected based on the modified correction data record.

10 Claims, 2 Drawing Sheets

CORRECTION METHOD AND MAGNETIC RESONANCE DEVICE

CROSS REFERENCE TO RELATED APPLICATIONS

This application claims priority of German application No. 10 2008 020 781.0 filed Apr. 25, 2008, which is incorporated by reference herein in its entirety.

FIELD OF THE INVENTION

The invention relates to a correction method for the correction of noise resulting from gradient artifacts in the ECG signal data records, and to a magnetic resonance device with which the correction method can be performed.

BACKGROUND OF THE INVENTION

ECG measuring apparatuses are primarily used for the measurement and monitoring of the cardiac function of a patient, and typically the total voltage of the electrical activity in the cardiac muscle fibers is measured as the so-called "ECG signal" via at least two electrodes.

However there are also further applications. For example ECG signals are also used in medical imaging to generate trigger signals. During imaging, information about the cardiac phase is obtained via the ECG signal in order thereby to synchronize the imaging with the cardiac activity. Particularly in the case of imaging procedures that require a longer recording time, cardiac recordings, or indeed recordings of areas that are moved by the heartbeat, can be produced to a high quality in this way.

ECG measuring apparatuses are also used for the in-situ recording of ECG signals during an examination of a patient by means of a magnetic resonance device. On account of the strong gradient fields and high-frequency fields used in the magnetic resonance device, however, particular demands are placed in this case on the ECG measuring apparatus by an operation in the magnetic resonance device, in order to prevent reciprocal interference between the magnetic resonance device and the ECG measuring apparatus. ECG measuring apparatuses, which are magnetic-resonance-compatible within the meaning described above, are available on the market.

However magnetic fields that vary over time, such as those used in the magnetic resonance device as magnetic gradient fields for position encoding, continue to pose a major problem for reliable ECG signal measurement. In accordance with the law of induction such magnetic fields that vary over time generate noise voltages that are coupled into the ECG signal recorded by the ECG electrodes as noise. Magnetically-generated noise signals of this type are superimposed on and corrupt the ECG signal generated by the heart. A signal data record $U1(t)$ measured at a first channel of the ECG measuring apparatus then contains not only the desired ECG signal U1 EKG(t) at the time t, but also a superposition of the ECG signal with the noise voltages $S1(t)$ generated by induction at the time t:

$$U1(t) = U1\ EKG(t) + S1(t).$$

This noise is highly undesirable. In order to synchronize a recording of a magnetic resonance image with the heartbeat, a reliable identification of the R-wave in the ECG signal is required. The noise signals can be interpreted erroneously as an R-wave e.g. on account of their often similar shape, and can thus cause a magnetic resonance image to be recorded spuriously. On the other hand it may also be the case that a "real" R-wave is not recognized as such on account of the superimposed noise signals. This frequently causes a considerable deterioration in image quality.

From the publications "Restoration of Electrophysiological Signals Distorted by Inductive Effects of Magnetic Field Gradients During MR Sequences"; Jacques Felblinger, Johannes Slotboom, Roland Kreis, Bruno Jung, Chris Boesch; Magnetic Resonance in Medicine 41:715-721 (1999) and "Noise Cancellation Signal Processing Method and Computer System for Improved Real-Time Electrocardiogram Artifact Correction during MRI Data Acquisition"; Freddy Odille, Cedric Pasquier, Roger Abächerli, Pierre-Andre Vuissoz, Gary P. Zientara, Jacques Felblinger; IEEE Transactions on Biomedical Engineering, VOL. 54, NO. 4, APRIL 2007, a method is known in which an estimation of the noise artifacts caused by the gradient fields and thus of the noise voltages is performed. The estimated noise voltage of an ECG channel $S1(t)$ est is then subtracted from the ECG signals $U1(t)$ measured on the same ECG channel in order to obtain a corrected ECG signal U1 korr(t):

$$U1\ korr(t) = U1\ EKG(t) + S1(t) - S1\ est(t).$$

It is assumed here that the noise voltages $S1(t)$ can be separated into noise voltages $S1x(t)$, $S1y(t)$ and $S1z(t)$, each of which is caused by the known currents $Ix(t)$, $Iy(t)$ and $Iz(t)$ that are impressed on the x-, y- and z-axis gradient coils:

$$S1(t) = S1x(t) + S1y(t) + S1z(t)$$
$$= h\ Ix\ U1(t) * Ix(t) + h\ Iy\ U1(t) * Iy(t) +$$
$$h\ Iz\ U1(t) * Iz(t).$$

where $h\ Ii\ U1(t)$ (i=x,y,z) represents the corresponding impulse response that characterizes the influence on the ECG signal $U1(t)$ exerted by the current Ii(t) through the i-axis gradient coil. "*" indicates a system-theoretical convolution.

Here the x-, y- and z-axes are perpendicular to each other, with the x-axis typically corresponding to a normal vector on a sagittal plane, the y-axis to a normal vector on a coronary plane, and the z-axis to a normal vector on a transverse plane, through a patient located in a magnetic resonance device.

The aforementioned impulse responses $h\ Ii\ U1(t)$ are estimated by measuring e.g. ECG signals $U1(t)$ in training measurements if in each case only one of the gradient coils is fed a current Ii(t) not equal to zero, such that the following applies e.g. where i=x:

$$U1(t) = U1\ EKG(t) + h\ Ix\ U1(t) * Ix(t).$$

The impulse response $h\ Ix\ U1(t)$ can be estimated from this equation by means of calculations in the frequency range. The contribution made by U1 EKG(t) can then be deducted e.g. by repeated measurement and subsequent averaging of $U1(t)$. The same procedure is performed for further impulse responses. The result is as follows:

$$S1\ est(t) = h\ Ix\ U1\ est(t) * Ix(t) + h\ Iy\ U1\ est(t) * Iy(t) + h\ Iz\ U1\ est(t) * Iz(t).$$

For more precise details, reference is made to the aforementioned prior art.

Good results are achieved with this method when ECG signals are corrected that were measured under the same conditions which also prevailed during the aforementioned training measurements. The results deteriorate when these conditions change e.g. through a change in the position of the patient and thus also of the ECG measuring apparatus in the magnetic resonance device, with the effect that new impulse responses that are adjusted to the changed conditions have to be estimated with the aid of further training measurements. In this way an examination of a patient would be disadvantageously extended and the stress experienced by the patient as a result of the examination would be increased.

SUMMARY OF THE INVENTION

The object of the invention is therefore to specify a correction method and a magnetic resonance device that enable a reliable and rapid correction of ECG signal data records measured in the magnetic resonance device, including under changed measuring conditions.

This object is achieved in accordance with the invention by a correction method and a magnetic resonance device as claimed in the claims.

An inventive correction method for the correction of noise resulting from gradient artifacts in ECG signal data records, which were recorded in a magnetic resonance device by means of an ECG measuring apparatus, thus comprises the following steps:

- Determining a first correction data record, with a reference point of the ECG measuring apparatus being located at a first position in the magnetic resonance device;
- Measuring an ECG signal data record to be corrected with the reference point of the ECG measuring apparatus at a second position in the magnetic resonance device;
- Specifying a modified correction data record as a function of the first correction data record and the second position of the reference point of the ECG measuring apparatus;
- Correcting the ECG signal data record to be corrected with the aid of the modified correction data record.

With the inventive correction method a correction data record initially determined at a first position can now be translated into a modified correction data record that applies at a second position. An additional determination of further impulse responses can be omitted without significantly compromising the quality of the correction. The inventive correction method thus helps to save time and improve the quality of magnetic resonance image recordings, since noise induced by magnetic fields can more easily be detected and suppressed, as a consequence of which a triggering of the magnetic resonance device upon the R-waves of an ECG signal can be performed more precisely, which results in a better image quality.

An inventive magnetic resonance device comprises an ECG measuring apparatus, a position-recording unit for recording a position of a reference point of the ECG measuring apparatus, and a correction data record determining unit for determining first and modified correction data records that interact such that an inventive correction method can be performed with the magnetic resonance device.

The method-related advantages apply analogously for a magnetic resonance device according to the invention.

BRIEF DESCRIPTION OF THE DRAWINGS

Further advantages and details of the present invention will emerge from the exemplary embodiments described below and with the aid of the drawings. Examples are provided below, which do not constitute any limitation of the invention, and in which.

DETAILED DESCRIPTION OF THE INVENTION

Figure 1:
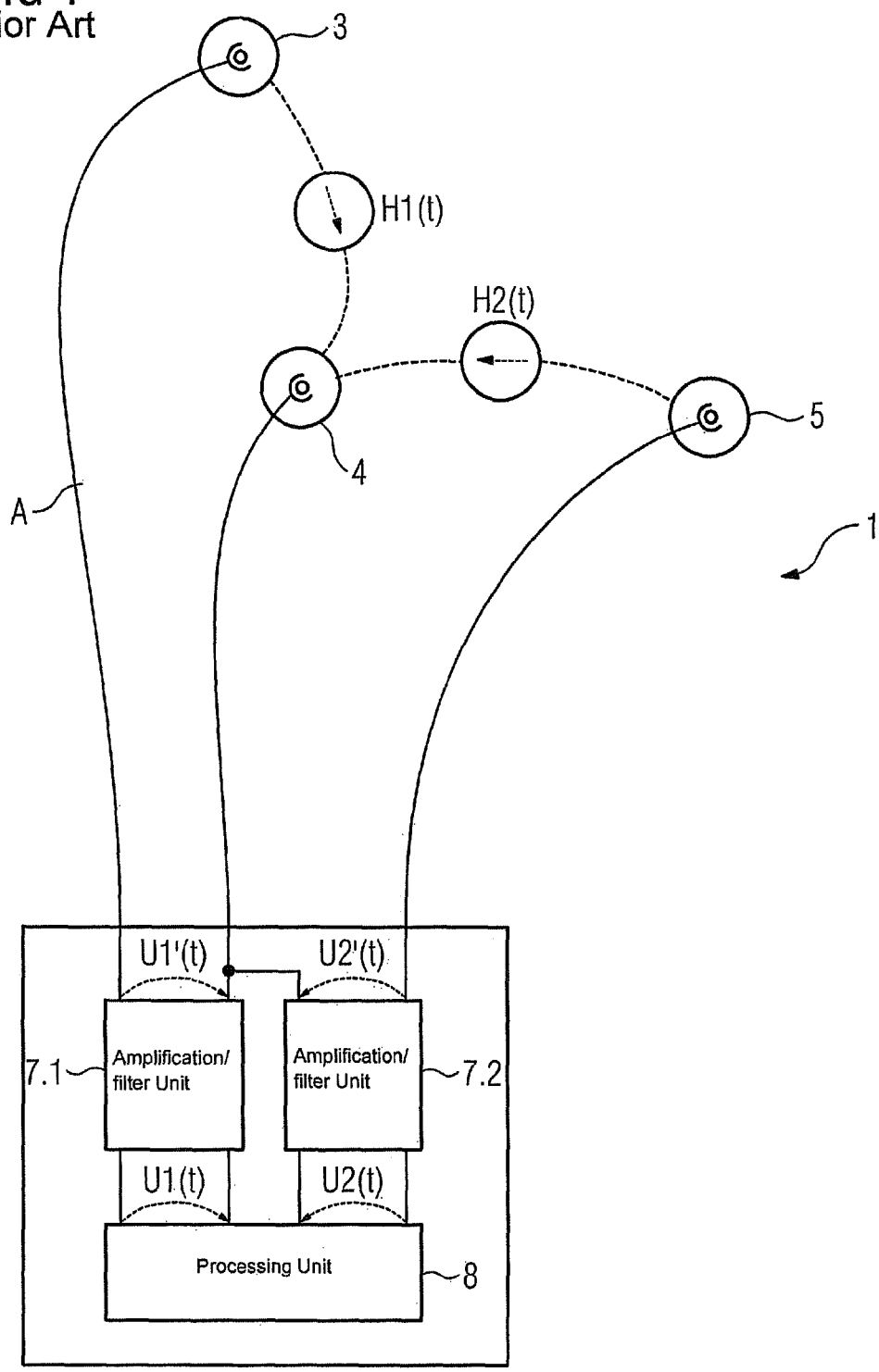
FIG. 1 shows a schematic view of a conventional ECG measuring apparatus in order to illustrate the problem.

In order to illustrate the basic problem underlying the invention and in order to introduce the parameters used below, FIG. 1 shows a schematic view of a conventional ECG measuring apparatus 1, here comprising three electrodes 3, 4, 5 attached to a patient (not shown) in the usual manner. Each of the two electrodes, here e.g. 3 and 4, or 4 and 5, are connected via cables to an amplification/filter unit 7.1 and 7.2 respectively. The amplification/filter units 7.1 and 7.2 each measure the voltages U1'(t) and U2'(t) present between the incoming cables and conduct said voltages as ECG signals U1($t$) and U2($t$) to a unit 8 for further processing, in which the signals can be e.g. converted into digital signals, stored and/or processed in some other way.

The amplification/filter units 7.1 and 7.2 can be described in system-theoretical terms by their impulse responses h U'U1($t$) and h U2'U2($t$), where:

$$U1(t) = U1'(t) * h\, U1'U1(t) \text{ and}$$

$$U2(t) = U2'(t) * h\, U2'U2(t)$$

A voltage H1($t$) generated by the dipole field of the heart is applied between the electrodes 3 and 4. A voltage H2($t$) is applied analogously between the electrodes 4 and 5.

In an ideal scenario H1($t$)=U1'(t) and H2($t$)=U2'(t). However, as just described above, time-variable magnetic fields, such as gradient fields especially for position encoding of magnetic resonance recordings, couple into the current paths formed by the electrodes and their cables as noise voltages, so that in the case of the signals Uj(t)(j=1,2) measured at the channels j of the ECG measuring apparatus 1, the following applies:

$$\begin{aligned} Uj(t) &= Uj\, EKG(t) + Sj(t) \\ &= Hj(t) * h\, Uj'\, Uj(t) + h\, Ix\, Uj(t) * Ix(t) + h\, Iy\, Uj(t) * \\ &\quad Iy(t) + h\, Iz\, Uj(t) * Iz(t) \end{aligned}$$

Although the method is always described below with the aid of the example of an ECG measuring apparatus 1 with three electrodes 3, 4, 5 and two ECG channels j=1,2 as shown in FIG. 1, said method is not limited to this example, but instead can be extended analogously to ECG measuring apparatuses with more than three electrodes and/or more than two channels j=1 ... N.

As has also already been described above, a method that estimates the noise voltages Sj(t) under given circumstances is known in the prior art. For this purpose the impulse responses h Ii Uj est(t) (i=x,y,z; j=1,2) must be estimated with the aid of training measurements. The estimated noise voltages Sj est(t) obtained in this manner represent correction data records with which the ECG signals Uj(t) can be corrected by subtracting the estimated noise voltages Sj est(t)

from the measured ECG signals Uj(t). This works well, as long as the position of the ECG measuring apparatus within the magnetic resonance device remains the same during recording of the ECG signals Uj(t) as during the training measurements.

If the ECG measuring apparatus is moved in the intervening time e.g. through a movement of a couch for the magnetic resonance device and thus a movement of the patient located thereon with the ECG measuring apparatus attached thereto, the impulse responses for the new position must be re-estimated.

Provision is now made in accordance with the invention to determine a modified correction data record 16 from the correction data record 14 determined first at a first position, with said correction data record 14 being based on impulse responses h1 Ii Uj est(t) (i=x,y,z; j=1,2) estimated at this first position, and from a known second position, with said modified correction data record 16 being applicable for a correction of ECG signals recorded at this second position, without having to perform a re-estimation.

In order to explain how the determination of the modified correction data records 16 is to proceed, we will first consider the example of an impulse response h Ix U1($t$).

This can be modeled in system-theoretical terms and thus divided into a first sub-system and a second sub-system. The first sub-system describes how the current Ix(t) is transformed by the x-axis gradient coil into a magnetic field B, which through its transformation induces a voltage U1 ind(t) in the current path of the electrodes 3 and 4, with said voltage being superimposed over the voltage H1($t$) generated by the dipole field of the heart at the input of the amplification/filter unit 7.1. The second sub-system models the impulse response of the amplification/filter unit 7.1. The following thus applies:

$$h\ Ix\ U1(t) = h\ Ix\ U1'(t) * h\ U1'U1(t).$$

where the second sub-system is the impulse response h Ix U1($t$), in other words h U1' U1($t$), irrespective of the patient and the ECG measuring apparatus and their position in the magnetic resonance device. In what follows it is therefore sufficient to consider just the impulse response of the first sub-system h Ix U1'(t).

The current Ix(t) enters a magnetic field Bx(x,y,z,Ix(t)) generated by the current Ix(t) by means of the x-axis gradient coil in a linear fashion (analogously for By and Bz). As described, the voltage U1'(t) at the input of the amplification/filter unit 7.1 is composed of the voltage H1($t$) generated by the dipole field of the heart and the voltage U1 ind(t) induced by the respective flow of current into the x-, y- and z-axis gradient coils:

$$U1'(t) = H1(t) + U1\ ind(t)$$
$$= H1(t) - \left( \oint\int_A Bx(x, y, z, Ix(t)) \cdot da + \oint\int_A By(x, y, z, Iy(t)) \cdot da + \oint\int_A Bz(x, y, z, Iz(t)) \cdot da \right).$$

where A is the surface that is surrounded by the current path of the electrodes 3 and 4, i.e. by the cables of the electrodes 3 and 4 and by the voltage taps H1($t$) and U1'(t). Since the currents enter the B fields in a linear fashion and are independent of the positional coordinates x,y,z, it can be stated that:

$$U1'(t) = H1(t) + Ix(t) \cdot \underbrace{\oint\int_A fx(x, y, z) \cdot da}_{Kx} +$$
$$Iy(t) \cdot \underbrace{\oint\int_A fy(x, y, z) \cdot da}_{Ky} + Iz(t) \cdot \underbrace{\oint\int_A fz(x, y, z) \cdot da}_{Kz}$$

where fx(x,y,z), fy(x,y,z) and fz(x,y,z) are vector-valued functions that specify the field characteristics of the x-, y- and z-axis gradient coils at any coordinates, the amplitude of which at any coordinate is proportional to the strength of the corresponding magnetic field.

In accordance with the considerations above, the impulse responses h Ix U1($t$), h Iy U1($t$), h Iz U1($t$) are proportional to the coupling coefficients Kx, Ky, Kz. The integrals above are accordingly simply a function of the shape of the surface A and its position within the magnetic field.

If, before and after a repositioning of the patient, e.g. through a movement of the patient couch in the z direction, the surface A is located in the range of linearity of all three gradient coils, the equation above can be stated as follows:

$$U1'(t) = H1(t) + Ix(t) \cdot \underbrace{\oint\int_A fx(x) \cdot da}_{Kx} +$$
$$Iy(t) \cdot \underbrace{\oint\int_A fy(y) \cdot da}_{Ky} + Iz(t) \cdot \underbrace{\oint\int_A fz(z) \cdot da}_{Kz}$$

In other words fx, fy, fz are each a function of x, y, z.

Thus if there is a change in position in just one of the spatial directions x,y,z, for example only in the z direction, each of the other coupling coefficients Kx und Ky and therefore the corresponding impulse responses h Ix U1'(t), h Iy U1'(t) and h Ix U1($t$), h Iy U1($t$) do not change.

Figure 2:
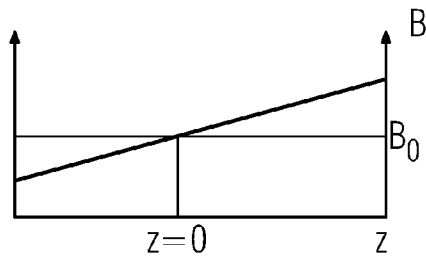
FIG. 2 shows the course of a gradient field by value in the z direction.

Typically the strength of the gradient magnetic fields rises in a linear fashion in the corresponding direction. Accordingly the value of the function fz(z) in the range of linearity obeys the following law:

$$|fz(z)| = N z.$$

where the parameter N specifies the incline in the gradient field in the direction of the gradient (here the z direction). The incline in the gradient fields is in each case known as a system parameter of a measurement with the magnetic resonance device. Furthermore the coordinate system is positioned such that the above value function has its zero point at z=0 as shown in FIG. 2.

For a first position z0 it can therefore be stated that:

$$Kz0 = N \cdot \oint\int_{Az0} z \cdot Z \cdot da.$$

where Z is a vector of length 1 that points in the z direction. Az0 represents the surface surrounded by the current path, where a selected reference point of the ECG measuring apparatus, e.g. the electrode 4, is located at the position of the coordinate z0.

For the second position z1 it can analogously be stated that:

$$Kz1 = N \cdot \oint \int_{A_{z1}} z \cdot Z \cdot da.$$

where Az1 represents the surface surrounded by the current path, where the reference point of the ECG measuring apparatus is located at the position of the coordinate z1.

Generating the quotient of the coupling coefficients Kz1 and Kz0 yields the following:

$$\frac{Kz1}{Kz0} = \frac{N \cdot \oint \int_{A_{z1}} z \cdot Z \cdot da}{N \cdot \oint \int_{A_{z0}} z \cdot Z \cdot da} = \frac{z1 \cdot \oint \int_{A_0} Z \cdot da + \oint \int_{A_0} z \cdot Z \cdot da}{z0 \cdot \oint \int_{A_0} Z \cdot da + \oint \int_{A_0} z \cdot Z \cdot da} \approx \frac{z1}{z0}.$$

where in the second step a coordinate shift is performed in order to bring each of the boundaries of the integrals to the surface A0 surrounded by the current path, where the reference point of the ECG measuring apparatus is located at the position of the coordinate z=0.

The approximation applied in the third and final step is particularly applicable if z0 and z1 are considerably greater than the measurements of the surface A0. In other words, if the surface A0 extends in the z direction from z=0 to z=δz, the following should apply:

$z0 >> \delta z$ and $z1 >> \delta z.$

Thus the value of the impulse response h Iz U1'(t) is accordingly proportional to Kz. As a good approximation, Kz is in turn proportional to the position z itself The result of this is therefore that, as a good approximation, the value of the impulse response h Iz U1'(t) is proportional to the position z.

From a correction data record 14 determined first at a first position z0, with said correction data record 14 being based on the impulse responses h1 Iz Uj est(t) (j: channel) estimated at this first position z0, and a known second position z1, it is therefore now easily possible to determine a modified correction data record 16 by multiplying an estimated impulse response h1 Iz Uj est(t) of the first correction data record 14 by the factor z1/z0 in order to determine a second impulse response h2 Iz Uj est(t):

$$h2 \; Iz \; Uj \; est(t) = \frac{z1}{z0} h1 \; Iz \; Uj \; est(t).$$

Impulse responses estimated first at the position z0 e.g. for two channels U1(t) and U2(t), on which a first correction data record 14 is based: h Ix U1 est(t), h Iy U1 est(t), h Iz U1 est(t) and h Ix U2 est(t), h Iy U2 est(t), h Iz U2 est(t), can thus be translated, after the position of the ECG measuring apparatus in the magnetic resonance device has been moved in the z direction, into a second set of impulse responses h2 Ii Uj est(t), which apply at the position z1, in order to determine a modified correction data record 16: h Ix U1 est(t), h Iy U1 est(t), z1/z0 h Iz U1 est(t) and h Ix U2 est(t), h Iy U2 est(t), z1/z0 h Iz U2 est(t).

Impulse responses no longer all need to be re-estimated. In this estimation it must of course be the case that z0≠0, although generally this does not really constitute a limitation. An analogous procedure can be performed with the other spatial directions x and y.

As described above a second set of noise voltages S2j est(t) can now once again be calculated easily, from the set of second impulse responses determined in this way, by representing the total above i of the convolutions of the respective impulse responses h2 Ii Uj est(t) with the corresponding current Ii(t), whereby said second set of noise voltages S2j est(t) represents the modified correction data record 16 and can be subtracted from ECG signal data records to be corrected, for the correction of same. An ECG signal data record comprises for example ECG signals of various channels of an ECG measuring apparatus.

Figure 3:
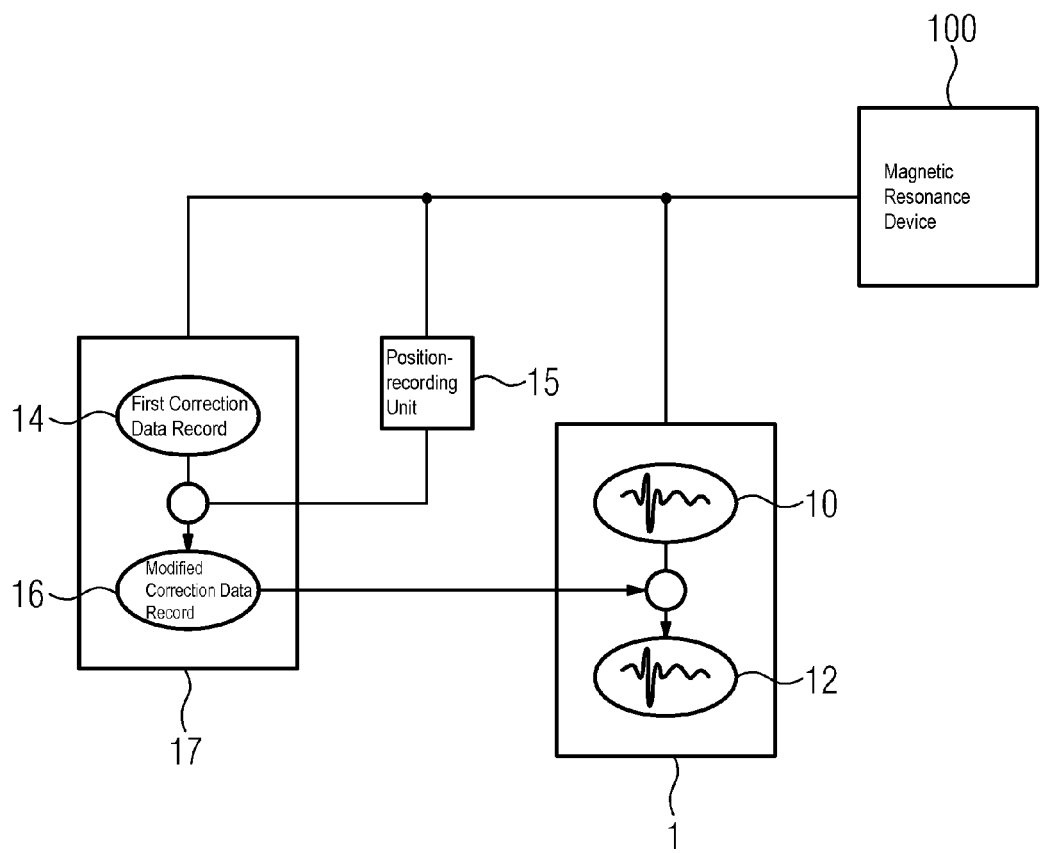
FIG. 3 shows a schematic view of a flow of the correction method according to the invention in connection with the magnetic resonance device according to the invention.

FIG. 3 shows a schematic view of a flow of the correction method according to the invention in connection with the magnetic resonance device according to the invention.

During an examination a patient with an attached ECG measuring apparatus 1 is located in the magnetic resonance device 100. Here the magnetic resonance device 100 is shown merely schematically as a block, since the basic configuration, comprising magnet unit, high frequency coils, gradient coil unit, couch, control units in particular also for controlling the couch, etc., is already known.

According to the invention the magnetic resonance device 100 comprises in particular an ECG measuring apparatus 1, a position-recording unit 15 and a correction data record determining unit 17. The separated presentation of these units is not necessarily physical and should be understood rather as a separation into logical units.

The ECG measuring apparatus 1, the position-recording unit 15 and the correction data record determining unit 17 are connected to the magnetic resonance device 100 and to each other for the transmission of data.

ECG signals 10 of a patient can be measured and processed with the ECG measuring apparatus 1. More detail has already been provided above in relation to FIG. 1. The position-recording unit 15 serves in particular to determine a position of the ECG measuring apparatus 1 or of a reference point of the ECG measuring apparatus 1 in the magnetic resonance device 100. To this end the position-recording unit 15 can for example access data from a preparatory measurement, e.g. from a so-called "localizer measurement", or data from a position determination via a light-beam localizer of the magnetic resonance device 100 or similar, and/or data about the current position of the couch of the magnetic resonance device 100.

The correction data record determining unit 17 allows for a first correction data record 14 to be determined in accordance with the prior art as described above. The correction data record determining unit 17 is furthermore connected to the position-recording unit 15 in order to receive data about the positions of the ECG measuring apparatus 1.

The transmitted position data comprises in particular a position of the ECG measuring apparatus 1 while the first correction data record 14 is being determined, and a position of the ECG measuring apparatus 1 during a measurement of an ECG signal 10 that is contaminated with noise artifacts. In accordance with the method described above the correction data record determining unit 17 can determine a modified correction data record 16 from the position data obtained and from the first correction data record 14.

The modified correction data record 16 can be transmitted via a further connection to the ECG measuring apparatus 1 and as has already been described above can be used there for the correction of an ECG signal 10 that is contaminated with gradient fields that vary over time, as a result of which a corrected ECG signal 12 is obtained in which the noise artifacts are largely eliminated.

The corrected ECG signal 12 can now be used for the secure triggering of recordings of the magnetic resonance device 100.

The invention claimed is:

1. A correction method for correcting a noise resulting from a gradient artifact in an ECG signal data record recorded in a magnetic resonance device by an ECG measuring apparatus, comprising:
   determining a correction data record from a first signal acquired by the ECG measuring apparatus when said ECG measuring apparatus is located at a first position relative to the magnetic resonance device, wherein the correction data record is based on estimating a first impulse response at the first position of the ECG measuring apparatus;
   recording the ECG signal data record to be corrected from a second signal acquired by the ECG measuring apparatus when said ECG measuring apparatus is located at a second position relative to the magnetic resonance device, the second position being spaced apart from the first position;
   determining with a processor a modified correction data record as a function of the correction data record and the first and the second position of the ECG measuring apparatus, wherein the determining of the modified correction data record is based on estimating a second impulse response defined by a product of a) the first impulse response at the first position of the ECG measuring apparatus time and b) a quotient $$\frac{z1}{z0},$$

wherein $z0$ represents a coordinate indicative of the first position of the ECG measuring apparatus, and further wherein $z1$ represents a coordinate indicative of the second position of the ECG measuring apparatus; and
   correcting the noise in the ECG signal data record from the second signal acquired by the ECG measuring apparatus at the second position, the correcting based on the modified correction data record without having to estimate a further impulse response at the second position.

2. The correction method as claimed in claim 1, wherein the first estimated impulse response is arranged to characterize an influence of the gradient artifact in the ECG signal data record.

3. The correction method as claimed in claim 1, wherein the correction data record is determined based at least in part on a known parameter of the gradient artifact.

4. The correction method as claimed in claim 3, wherein the known parameter of the gradient artifact comprises a current impressed on a gradient coil of the magnetic resonance device.

5. The correction method as claimed in claim 1, wherein the modified correction data record indicates the noise and is subtracted from the ECG signal data record for correcting the noise.

6. The correction method as claimed in claim 1, wherein the correction data record is determined by a training measurement at the first position.

7. The correction method as claimed in claim 6, wherein the training measurement is a preparatory measurement performed prior to an examination for adjusting the magnetic resonance device.

8. The correction method as claimed in claim 1, wherein the first correction data record and the modified correction data record are determined by at least one convolution of an impulse response with a parameter that causes the gradient noise.

9. The correction method as claimed in claim 1, wherein the ECG measuring apparatus comprises at least two ECG channels.

10. A magnetic resonance device, comprising:
   a magnet unit;
   high frequency coils;
   a gradient coil unit;
   an ECG measuring apparatus configured to record an ECG signal data record from a second signal acquired by the ECG measuring apparatus at a second position relative to the magnetic resonance device;
   a position-recording unit configured to record movement of the ECG measuring apparatus relative to the magnetic resonance device; and
   a correction data record determining unit configured to:
      determine a correction data record from a first signal acquired by the ECG measuring apparatus when said ECG measuring apparatus is located at a first position relative to the magnetic resonance device, the first position being spaced apart from the second position, wherein the correction data record is based on an estimation of a first impulse response at the first position of the ECG measuring apparatus,
      determine a modified correction data record as a function of the correction data record and the first and the second position of the ECG measuring apparatus, wherein a determination of the modified correction data record is based on an estimation of a second impulse response defined by a product of a) the first impulse response at the first position of the ECG measuring apparatus time and b) a quotient $$\frac{z1}{z0},$$

wherein $z0$ represents a coordinate indicative of the first position of the ECG measuring apparatus, and further wherein $z1$ represents a coordinate indicative of the second position of the ECG measuring apparatus, and
      correct the noise in the ECG signal data record from the second signal acquired by the ECG measuring apparatus at the second position, wherein the noise correction is based on the modified correction data record without having to estimate a further impulse response at the second position.

* * * * *